United States Patent [19]

Stingl

[11] 3,961,052

[45] June 1, 1976

[54] FUNGICIDAL COMPOSITIONS

[75] Inventor: Helmut Stingl, Hofheim, Taunus, Germany

[73] Assignee: Hoechst Aktiengesellschaft, Frankfurt am Main, Germany

[22] Filed: Dec. 3, 1974

[21] Appl. No.: 529,119

Related U.S. Application Data

[63] Continuation-in-part of Ser. No. 356,404, May 2, 1973, abandoned.

[30] Foreign Application Priority Data

May 5, 1972 Germany............................ 2222133

[52] U.S. Cl................................ 424/200; 424/273; 424/308
[51] Int. Cl.² ...................... A01N 9/02; A01N 9/22; A01N 9/36
[58] Field of Search..................... 424/200, 273, 308

[56] References Cited
UNITED STATES PATENTS 3,632,757  1/1972  Scherer et al........................ 424/200

FOREIGN PATENTS OR APPLICATIONS 1,190,614  5/1970  United Kingdom

*Primary Examiner*—Jerome D. Goldberg
*Assistant Examiner*—Allen J. Robinson
*Attorney, Agent, or Firm*—Curtis, Morris & Safford

[57] ABSTRACT

Pesticidal compositions containing as active ingredients 2-(O,O-diethyl-thionophosphoryl)-5-methyl-6-carbethoxy-pyrazolo-(1,5a)-pyrimidine in admixture with (a) 2-methoxycarbonylamino-benzimidazole or (b) 1-(N-butylcarbamoyl)-2-methoxycarbonyl-aminobenzimidazole or (c) 1,2-bis(3-ethoxycarbonyl-2-thioureido)-benzene or (d) 1,2-bis-(3-methoxycarbonyl-2-thioureido)-benzene or (e) 1-(3-methoxycarbonyl-2-thioureido)-2-aminobenzene have a synergistic effect against phytopathogenic fungi.

11 Claims, No Drawings

FUNGICIDAL COMPOSITIONS

This application is a continuation-in-part of our co-pending application Ser. No. 356,404 filed May 2, 1973, now abandoned.

The present invention relates to pesticidal compositions containing as active ingredient 2-(O,O-diethyl-thionophosphoryl)-5-methyl-6-carbethoxy-pyrazolo-(1,5a)-pyrimidine of the formula I

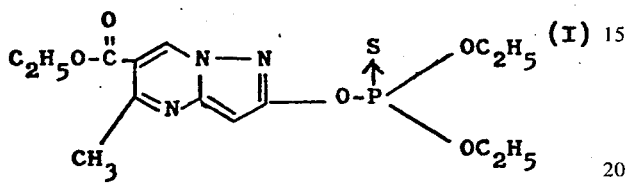

in admixture with a. 2-methoxycarbonylamino-benzimidazole of the formula II

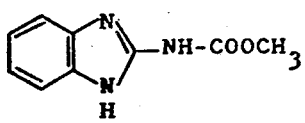

or b. 1-(N-butylcarbamoyl)-2-methoxycarbonyl-amino-benzimidazole of the formula III

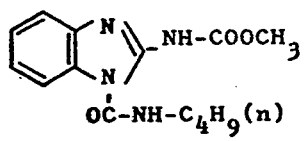

or c. 1,2-bis(3-ethoxycarbonyl-2-thioureido)-benzene of the formula IV

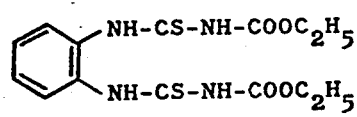

or d. 1,2-bis(3-methoxycarbonyl-2-thioureido)-benzene of the formula V

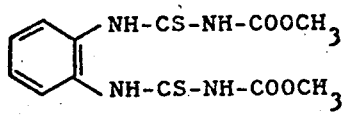

or e. 1-(3-methoxycarbonyl-2-thioureido)-2-aminobenzene of the formula VI.

The compound of formula I is known from German Pat. No. 1,545,790 and is used as a fungicide mainly against mildew. The compounds of formulae II to VI as well as their fungicidal effect are likewise known (II: U.S. Pat. No. 3,010,968; III: Netherlands specification Pat. No. 6,706,331; IV and V: German Offenlegungsschrift No. 1,806,123; Japanese Pat. No. 638,021).

It has now been found that mixtures of compound I with compounds II, III, IV, V, or VI, respectively, have not only an additive but a synergistic effect against phytopathogenic fungi. The synergistic effect is observed with mixing ratios in the range of from 10 : 1 to 1 : 10, expecially 5 : 1 to 1:5.

With the mixture of active ingredients according to the invention the same effect as obtained with the individual components can be achieved with lower concentrations. Moreover, the danger of resistency as observed with the use of benzimidazole compounds is considerably reduced with the compositions of the invention.

The compositions of the invention can be used successfully against a plurality of phytopathogenic fungi, especially against genuine mildew, as well as against ascomycetes and fungi imperfecti. By way of example, the following may be named: Venturia inaequalis causing apple scab, Podosphaera leucotricha causing apple mildew and Botrytis cinerea causing botrytis disease in fruit.

When applied in suitable dosage the compositions of the invention have a protective as well as curative effect. They are especially suitable for combating or preventing fungus diseases in living plants, for example in orchards and nurseries, fancy plants, vegetables, shrubs, cereals, salad, potatoes, and the like.

The compositions of the invention can be applied in the form of wettable powders, dusting powders, granules and advantageously in the form of dispersions in paraffinic or vegetable oils, or suitable higher boiling liquid organic dispersion media such as ethers and esters, preferably phthalic acid esters, for example phthalic acid diisooctyl ester. The active compound I is suitably incorporated into the dispersions as a solution in an aromatic solvent.

In the preparation of wettable powders and dusts the active compound I is first adsorbed on finely dispersed carrier materials, such as synthetic silicic acids, diatomaceous earth, or bentonites, and then ground together with one of the active compounds II to VI, a further amount of carrier material and dispersing agents, wetting agents and adhesives. In the preparation of dusts, talc or calcium silicates and clays are expediently used as carrier material.

Granules are preferably prepared by impregnating an inert granular carrier material, for example quartz sand, with a solution of active compound I in a high boiling solvent, for example high boiling fractions of aromatic hydrocarbons, ketones, for example isophorone, advantageously in the presence of an emulsifier and a stabilizer, and applying on the wetted sand one of the active compounds II to VI in finely ground form, while drying the granules. Alternatively, a solution of the active compound I is applied to an absorbent granular carrier material, for example attapulgite, and a ground powder of one of the active compounds II to VI is applied on the said granules.

Suitable dispersing agents present in the wettable powders are the sodium salts of dinaphthylmethane-disulfonic acid, of dialkyl-naphthalene-sulfonic acids, of oleylmethyl-tauride as well as alkali metal and alkaline earth metal salts of ligninsulfonic acids, or sodium salts of sulfosuccinic acid esters. Suitable wetting agents are sodium dodecyl-benzenesulfonates or polyethylene or polypropylene glycols adsorbed on synthetic silicic acids. Suitable adhesives are partially saponified polyvinyl acetates, polyvinyl alcohols, polyvinyl-pyrrolidones, carboxyethyl cellulose, hydroxyethyl cellulose, as well as vegetable gums.

The following organic dispersion media are suitable for the formulation of liquid dispersions: O-acyl- and nonyl-phenol polyglycol ethers, triisobutyl-phenol polyglycol ether, castor oil polyglycol ethers or esters, preferably in the presence of a calcium salt of dodecyl-benzenesulfonic acid. Depending on the chain length of the aforesaid polyglycol ethers or esters, these substances are more or less suitable as dispersion agents in paraffin oils, vegetable oils or other organic liquid dispersion media.

Owing to the high boiling point of the organic dispersion media the dispersions are well suitable for an application according to the ultra-low-volume process, the more so as the formulations can easily be diluted with water or further organic liquids, such as fractions of paraffin oils, without the active ingredient flocculating.

The pesticidal compositions of the present invention can contain 2 to 70 % by weight of the mixture of the active ingredients. To ensure a satisfactory handling and good fluidity of the dispersions, they contain of from 10 to 40 % by weight, preferably 20 to 25 % of the mixture of active ingredients. Wettable powders may contain up to 70 %, granules 2 to 20 % and dusts 2 to 10 % by weight of the mixture of active ingredients.

The following examples illustrate the invention.

EXAMPLE 1

A dispersion in paraffin oil is obtained by finely grinding in a grinding ball mill:
15.0 % by weight of active compound II
3.0 % by weight of active compound I
0.07 % by weight of epichlorohydrin
7.50 % by weight of nonyl-phenol polyglycol ether
3.25 % by weight of triisobutyl-phenol polyglycol ether
2.65 % by weight of calcium dodecyl-benzenesulfonate
0.70 % by weight of ricinol polyglycol ether or ester
8.33 % by weight of xylene
59.5 % by weight of paraffin oil.

EXAMPLE 2

A wettable powder is composed of:
30.0 % by weight of active compound II
15.0 % by weight of active compound I
7.5 % by weight of paraffin-containing aromatic oil (Mobilsol F of Mobil Oil AG)
37.0 % by weight of finely dispersed silicic acid
5.0 % by weight of sodium dinaphthalene-disulfonate
2.0 % by weight of sodium dibutylnaphthalene-disulfonate
0.5 % by weight of epichlorohydrin
2.0 % by weight of partially saponified polyvinyl acetate
1.0 % by weight of polypropylene glycol

EXAMPLE 3

A granular composition containing 5.75 % of total active ingredients is obtained as follows:
91.275 % by weight of quartz sand (particle size 0.3 to 1 mm) are wetted with a solution of 0.75 % by weight of active compound I in 0.75 % by weight of aromatic oil (Mobilsol F Mobil Oil AG) and 0.025 % by weight of epichlorochydrin.
In a mixer 7.20 % by weight of a finely ground mixture of 70 % of active compound II with silicic acid is applied by rolling onto the wet sand.

EXAMPLE 4

As comparative composition a 50 % wettable powder of active compound II is prepared as follows:
50 % by weight of active compound II
5 % by weight of sodium dinaphthylmethane-disulfonate
2 % by weight of sodium dibutylnaphthalene-sulfonate
2 % by weight of partially saponified polyvinyl acetate
1 % by weight of polypropylene glycol
19 % by weight of powdered skim milk
21 % by weight of synthetic finely dispersed silicic acid

EXAMPLE 5

As comparative composition a 30 % emulsion concentrate of active compound I is prepared from:
30 % by weight of active compound I
5.5 % by weight of ricinol-polyglycol ether
4.5 % by weight of calcium phenyl sulfonate
0.5 % by weight of epichlorohydrin
59.5 % by weight of xylene

EXAMPLE I

Cucumber plants grown in pots in the greenhouse were strongly infested in the two-leaf stage with a suspension of conidia of cucumber mildew (Erysiphe cichoriacearum D.C.) and kept for 1 day in a moisture chamber at 95 – 100 % of relative atmospheric humidity and at 20°C. Next, the plants were placed in the greenhouse at a temperature of 22°C and, after a period of 5 days, the infested plants were treated with combinations of active compounds I and II as specified in Table I. Care was taken that the leaves were well wetted. After drying of the layer of spray liquor the plants were again placed in the greenhouse and, after an incubation time, they were kept under observation until the untreated control plants showed a distinct layer of mildew. The degree of infestation with mildew was evaluated by visual inspection. The degree of infestation was ascertained according to the scheme of numbers 1 to 9 drawn up by the "Biologische Bundesanstalt in Braunschweig" (BBA), Federal Republic of Germany (see below). The synergistic effect of the combination of active compounds was evaluated by the method according to Horsfall or Sakai (cf. J. G. Horsfall "Fungicides and their action" Chronica Botanica, 1945, (Walham, Mass.), pages 239 et seq; Sakai et al. "Insect Toxicological Studies in the Joint Toxic Action of Insecticides between Contact Insecticides" Boty-Kagaku, 16 (1951), pages 130 – 140).

EXAMPLE II

In the manner described in Example I tests were carried out with mixtures of active compound I with compounds III, IV, V, and VI respectively. The results are indicated in the following Tables II to V.

| BBA Scheme: degree of efficiency (% of non infested leaf surface) | |
|---|---|
| 1 | 100 % |
| 2 | 97.5 % |
| 3 | 95 % |
| 4 | 90 % |
| 5 | 85 % |
| 6 | 75 % |
| 7 | 65 % |
| 8 | 32.5 % |
| 9 | 0 % |

TABLE I

| active compound I 30 % emulsion concentrate | Concentration applied* active compound II 50 % wettable powder | evaluated according to BBA scheme 6 repetitions | average | efficiency % of non-infested leaf surface |
|---|---|---|---|---|
| 0 | 0.003 % | 6 6 7 8 6 7 | 6.6 | 70 |
| 0.0006 % | + 0.0024 % | 5 5 3 4 3 3 | 3.8 | 92 |
| 0.0012 % | + 0.0018 % | 2 3 2 2 3 3 | 2.5 | 96 |
| 0.0018 % | + 0.0012 % | 4 3 2 3 3 3 | 3.0 | 95 |
| 0.0024 % | + 0.0006 % | 5 4 4 5 5 4 | 4.5 | 88 |
| 0.003 % | — | 5 5 6 5 6 6 | 5.5 | 80 |
| untreated | | 9 9 9 9 9 9 | 9 | 0 |

*The concentration applied refers to grams of 30 % emulsion concentrate and grams of 50 % of wettable powder per 100 ml of spray liquor that were applied. The ratio of compound 1 to 2 applied was 1:6,7 to 2,4:1.

TABLE II

| Concentration applied Compound I 30 % emulsion concentrate | Compound III 50 % wettable powder | evaluated according to BBA scheme 6 repetitions | average | efficiency (% of non-infested leaf surface) |
|---|---|---|---|---|
| 0 | 0.003 % | 5 5 6 6 5 4 | 5.2 | 81 |
| 0.0006 % | + 0.0024 % | 3 3 4 3 3 3 | 3.2 | 94 |
| 0.0012 % | + 0.0018 % | 2 2 3 3 2 3 | 2.5 | 96 |
| 0.0018 % | + 0.0012 % | 3 3 2 3 2 2 | 2.5 | 96 |
| 0.0024 % | + 0.0006 % | 4 5 4 5 5 4 | 4.5 | 87 |
| 0.003 % | | 5 6 5 5 5 6 | 5.4 | 80 |
| untreated | | 9 9 9 9 9 9 | 9.0 | 0 |

TABLE III

| Compound I 30 % emulsion concentrate | + | Compound IV 50 % wettable powder | evaluated according to BBA scheme 4 repetitions | average |
|---|---|---|---|---|
| | | 0.003 % | 5 6 5 5 | 5.25 |
| 0.0006 | + | 0.0024 | 4 3 4 4 | 3.75 |
| 0.0012 | + | 0.0018 | 3 4 2 3 | 3.00 |
| 0.0018 | + | 0.0012 | 5 5 5 5 | 5.00 |
| 0.0024 | + | 0.0006 | 6 6 5 6 | 5.75 |
| 0.003 | | | 7 6 6 7 | 6.5 |
| untreated | | | 9 9 9 9 | 9 |

TABLE IV

| Compound I 30 % emulsion concentrate | + | Compound V 70 % wettable powder | evaluated according to BBA scheme 4 repetitions | average |
|---|---|---|---|---|
| | | 0.003 | 3 2 2 3 | 2.25 |
| 0.0006 | + | 0.0024 | 1 1 1 1 | 1.0 |
| 0.0012 | + | 0.0018 | 2 3 2 3 | 2.25 |
| 0.0018 | + | 0.0012 | 3 4 3 3 | 3.25 |
| 0.0024 | + | 0.0006 | 4 5 5 4 | 4.50 |
| 0.003 | | | 7 6 6 7 | 6.50 |
| untreated | | | 9 9 9 9 | 9.0 |

TABLE V

| Compound I 36 % emulsion concentrate | + | Compound VI 50 % wettable powder | evaluated according to BBA scheme 4 repetitions | average |
|---|---|---|---|---|
| | | 0.003 | 3 3 3 3 | 3.0 |
| 0.0006 | + | 0.0024 | 2 1 1 1 | 1.25 |
| 0.0012 | + | 0.0018 | 2 3 2 2 | 2.25 |
| 0.0018 | + | 0.0012 | 3 4 3 4 | 3.5 |
| 0.0024 | + | 0.0006 | 4 5 5 4 | 4.5 |
| 0.003 | | | 7 6 6 7 | 6.5 |
| untreated | | | 9 9 9 9 | 9 |

EXAMPLE IV

Apple trees of the variety Jonathan were sprayed against apple scab (*Podosphaera leucotricha Salm.*) 10 times at intervals of 14 days each with a mixture of 1 part of active compound I and 2 parts of active compound II in a total concentration of 0.04 %, with the individual compounds each in a concentration of 0.04 % and, for comparison, with 0.05 % of binapacryl (4,6-dinitro-2,6-butylphenyl-beta-dimethyl acrylate). For each spraying about 2000 1/ha of spray liquor were used. At the end of the vegetation period in late autumn the number of infested shoot ends was counted. In Table VI is given the percentage of mildew infested terminal buds of a total number of 200 shoot ends for each tree.

TABLE VI

|  | concentration of active compound | infestation of shoot ends % |
|---|---|---|
| untreated | — | 56 |
| active compound I | 0.04 % | 20 |
| active compound II | 0.04 % | 24 |
| active compound I + active compound II (ratio 1:3) | 0.04 % | 14 |
| binapacryl | 0.05 % | 20 |

EXAMPLE V

The procecure as described in Example I was repeated using mixtures of compounds I and II in various proportions but containing the same total amount of active ingredients (I + II). The following results were obtained:

proportions of a mixture of active ingredients and carrier, said active ingredients comprising 2 to 70% by weight of said composition, said synergistic proportions of active ingredients consisting of a ratio of 10:1 to 1:10 of 2-(O,O-diethyl-thionophosphoryl)-5-methyl-6-carbethoxy-pyrazolo-(1,5a)-pyrimidine of the formula

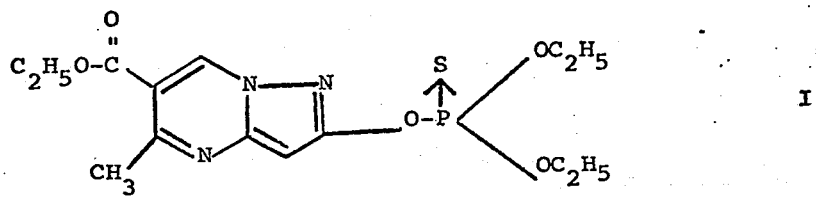

in admixture with 2-methoxycarbonylamino-benzimidazole of the formula

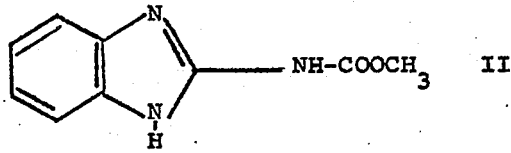

2. The composition of claim 1, containing the active ingredients in a ratio of from 5:1 to 1:5.
3. The composition of claim 1 containing 10 to 40% by weight of active ingredients dispersed in a liquid carrier.
4. The composition of claim 1 containing the mixture of active ingredients in dispersion in phthalic acid diisooctyl ester.
5. A method of combating phytopathogenic fungi that are infesting plants, which comprises applying to the fungi infested plants a fungicidally effective amount of the composition of claim 1.
6. A fungicidal composition comprising a fungicidally effective amount in synergistic proportions of a mixture of active ingredients and a carrier, said synergistic proportions of active ingredients consisting of a ratio of 10:1 to 1:10 of 2-(O,O-diethyl-thionophosphoryl)-5-

| total concentration in weight % compound I | compound II | sum (I + II) | weight proportion | evaluation acc. to BBA scheme (4 repetitions) | average | efficiency in % of non-infested leaf surface |
|---|---|---|---|---|---|---|
| — | 0.0011 | 0.0011 | — | 7 7 8 8 | 7,5 | 49 |
| 0.0001 | 0.0010 | 0.0011 | 1 : 10 | 6 5 6 6 | 5,75 | 72 |
| 0.00018 | 0.00092 | 0.0011 | 1 : 5 | 5 5 6 5 | 5,25 | 82 |
| 0.00055 | 0.00055 | 0.0011 | 1 : 1 | 4 5 4 5 | 4,5 | 87 |
| 0.00092 | 0.00018 | 0.0011 | 5 : 1 | 5 5 6 6 | 5,25 | 82 |
| 0.0010 | 0.0001 | 0.0011 | 10 : 1 | 6 5 5 6 | 5,5 | 80 |
| 0.0011 | — | 0.0011 | — | 6 6 6 6 | 6,0 | 75 |
| controls (untreated) | — | — | — | 9 9 9 9 | 9 | 0 |

What is claimed is:
1. A fungicidal composition comprising synergistic methyl-6-carbethoxy-pyrazolo-(1,5a)-pyrimidine of the formula

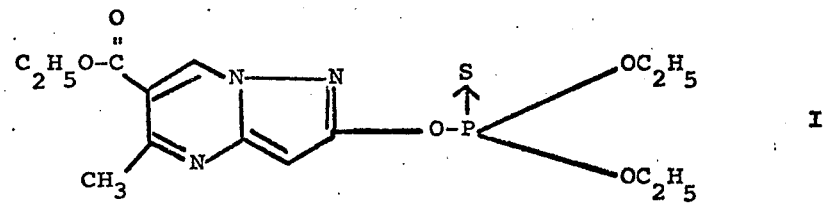

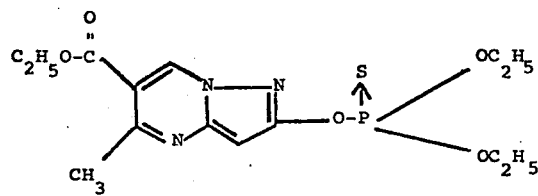

and
2-methoxycarbonylamino-benzimidazole of the formula

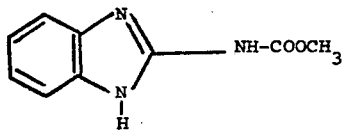

7. The fungicidal composition of claim 6 containing the active ingredients in a ratio of from 5:1 to 1:5.

8. The fungicidal composition of claim 6, containing the active ingredients in about equal amounts.

9. A method of combating fungi by applying to fungi, in a fungi infested area, a fungicidally effective amount of a composition comprising synergistic proportions of a mixture of active ingredients and a carrier, said synergistic proportions consisting of a ratio of 10:1 to 1:10 of 2-(O,O-diethyl-thionophosphoryl)-5-methyl-6-carbethoxy-pyrazolo-(1,5a)-pyrimidine of the formula and
2-methoxycarbonylamino-benzimidazole of the formula

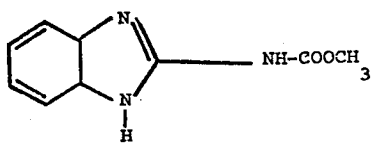

10. The method of claim 9, in which the composition contains 2 to 70% by weight of the active ingredients compounds I and II, the proportions of compounds I and II consisting of a ratio of about 5:1 to 1:5.

11. The method of claim 9 in which the composition contains the active ingredients in about equal amounts.

* * * * *